(12) United States Patent
Giesberg et al.

(10) Patent No.: US 6,462,868 B1
(45) Date of Patent: Oct. 8, 2002

(54) DISPLAY DEVICE FOR BOTH HARDCOPY AND DIGITAL IMAGES

(75) Inventors: Daniel Jay Giesberg, Los Angeles; David Irwin Lappen, Santa Monica; William Ascher Lappen, Encino, all of CA (US)

(73) Assignee: Buy-Phone, Inc., Encino, CA (US)

( * ) Notice: Subject to any disclaimer, the term of this patent is extended or adjusted under 35 U.S.C. 154(b) by 0 days.

(21) Appl. No.: 09/339,427

(22) Filed: Jun. 24, 1999

(51) Int. Cl.[7] .................. G03B 21/56; G03B 21/00; G02B 27/02

(52) U.S. Cl. .................. 359/443; 359/450; 359/449; 353/120; 40/361

(58) Field of Search ................. 359/447, 449, 359/450, 443; 353/11, 12, 28, 63, 64, 120; 40/553, 560, 361; 362/97, 311; 345/48, 50, 84, 87; 378/62; 382/132, 2

(56) References Cited

U.S. PATENT DOCUMENTS

| | | | |
|---|---|---|---|
| 4,059,767 A | * 11/1977 | Mocovski | 250/461.1 |
| 4,140,377 A | * 2/1979 | Hoadley | 353/78 |
| 5,430,964 A | * 7/1995 | Inbar et al. | 40/361 |
| 5,491,332 A | * 2/1996 | Inbar et al. | 382/212 |
| 5,544,654 A | 8/1996 | Murphy | 600/443 |
| 5,546,943 A | 8/1996 | Gould | 600/425 |
| 5,748,183 A | * 5/1998 | Yoshimura et al. | 345/173 |
| 5,790,216 A | * 8/1998 | Inbar et al. | 40/361 |
| 6,075,872 A | * 6/2000 | McGuire | 353/28 |
| 6,119,380 A | * 9/2000 | Inbar et al. | 40/361 |
| 6,269,565 B1 | * 8/2001 | Inbar et al. | 40/361 |
| 6,309,074 B1 | * 10/2001 | Inbar et al. | 40/361 |

FOREIGN PATENT DOCUMENTS

| | | |
|---|---|---|
| EP | 591 044 | 4/1994 |
| EP | 767417 A | 4/1997 |
| EP | 862 159 | 9/1998 |

* cited by examiner

Primary Examiner—Christopher Mahoney
(74) Attorney, Agent, or Firm—Crosby, Heafey, Roach & May

(57) ABSTRACT

A display device is provided which permits viewing of both hardcopy and digital images. An embodiment of an image viewing station comprises a housing having an internal light source and a light transmissive display panel coupled to the housing such that light from the internal light source passes therethrough. Hardcopy images affixed to an outer surface of the display panel may be transilluminated by the light passing through the display panel. Digital images may also be displayed on the display panel, by projecting the digital images onto either the inner or outer surface of the display panel. Alternatively, the panel could include a light emitting or light transmissive display panel, such as a liquid crystal display or an electroluminescent panel. Light emitted by the display panel may be sufficient to transilluminate a hardcopy image disposed on an outer surface of the display panel. A digital image is displayed on the same display panel by selectively driving the pixels of the display panel with digital image data. Alternatively, an internal light source may be included for transillumination of the hardcopy image or for improving backlighting of the digital images. The display panel may be selectively masked during hardcopy image viewing, and may further include sensors to detect presence, as well as size and position, of hardcopy images affixed to the display panel.

35 Claims, 4 Drawing Sheets

DISPLAY DEVICE FOR BOTH HARDCOPY AND DIGITAL IMAGES

BACKGROUND OF THE INVENTION

1. Field of the Invention

The present invention relates generally to image display devices, and more particularly, to methods and apparatus for displaying both digital images and images produced on transparent support materials intended to be viewed by transillumination.

2. Description of Related Art

In the medical industry, it is well known to use various types of imaging modalities to produce diagnostic images of structures and tissues contained within the body, such as x-ray, Magnetic Resonance Imaging (MRI), Computer Aided Tomography (CAT), ultrasound, etc. X-ray "hardcopy" images have been the traditional media used for image storage and recording. These hardcopy images are viewed by transillumination, using some form of rear-projected lighting that passes through a light-diffusing surface upon which the hardcopy image rests. The same process of transillumination is also used for other hardcopy image applications, such as in the graphic arts and printing industries. These transillumination viewing devices are often referred to as "viewboxes" or "illuminators". The light-diffusing surface of the viewboxes can be masked around the peripheral edges of a hardcopy image in order to block the light. It has been shown that "masking" the surrounding light so that it no longer hits the reader's eyes improves the reader's ability to distinguish fainter features on the hardcopy image, and therefore improves the reader's ability to make accurate diagnoses.

Newer imaging modalities, such as CAT, MRI and ultrasound, generate digital images that are provided to a digital workstation for display on a computer monitor. Similarly, in telemedicine, and specifically teleradiology, hardcopy images can be converted to their digital equivalent through the use of a scanning device for the purpose of transmitting the image to another site for evaluation. The digital workstations may include one or more separate monitors that can be individually controlled to manipulate and adjust the diagnostic image being displayed.

A drawback of the digital workstations is that they currently have no ability to view hardcopy images. Typical digital workstation display devices include some form of cathode ray tube that does not produce enough luminance to properly transilluminate a hardcopy image. Similarly, traditional viewboxes currently have no ability to display digital information. Although digital imaging is a small segment of the current market for image evaluation, it is clear that the market is in transition from hardcopy images to digital images. Nevertheless, it is unlikely that digital imaging will completely supplant hardcopy viewing in the foreseeable future. Perhaps more importantly, as in the case of transition from hardcopy to digital medical images, it will be necessary to review historical hardcopy images with current digital images in close proximity to each other.

It is therefore necessary that a medical facility have available separate and independent display devices.

Accordingly, it would be very desirable to provide a single display device that would permit display of both hardcopy and digital images. It would also be desirable to provide a display device that uses the same working surface to display either or both of these types of images. Moreover, it would be further desirable to provide a method to retrofit current viewboxes to also be able to display digital images and retrofit current display stations to also be able to display hard copy images.

SUMMARY OF THE INVENTION

The present invention overcomes the drawbacks of conventional image viewing systems by permitting both hardcopy and digital viewing in the same device.

In an embodiment of the invention, an image viewing station comprises a housing having an internal light source and a light transmissive display panel coupled to the housing such that light from the internal light source passes therethrough. Hardcopy images affixed to an outer surface of the display panel may be transilluminated by the light passing through the display panel. Digital images may also be displayed on the display panel, by projecting the digital images onto either the inner or outer surface of the display panel. The display panel may be selectively masked during hardcopy image viewing, and may further include sensors to detect presence, as well as size and position, of hardcopy images affixed to the display panel.

In another embodiment of the invention, an image viewing station comprises a light emitting or light transmissive display panel, such as a liquid crystal display or an electroluminescent panel. Light emitted by the display panel may be sufficient to transilluminate a hardcopy image disposed on an outer surface of the display panel. A digital image is displayed on the same display panel by selectively driving the pixels of the display panel with digital image data. Alternatively, an internal light source may be included for transillumination of the hardcopy image or for improving backlighting of the digital images. As in the first embodiment, the display panel can be selectively masked around the hardcopy image, and can include sensors to detect presence, size and position of hardcopy images affixed thereto.

The benefits of this invention are numerous and varied. First, as envisioned, for very little additional cost a "masked" transillumination element could be added to a digital display device. Second, by allowing both hardcopy and digital images to be simultaneously displayed in the same device, a diagnostician can perform comparison studies of differing modalities easily and in close proximity. Third, a combined device will eliminate the need to support dual systems with their attendant additional service and support cost, will free up valuable and scarce physical space, and eliminate the need for duplicate lighting, masking and control elements.

A more complete understanding of the display device for both hardcopy and digital images will be afforded to those skilled in the art, as well as a realization of additional advantages and objects thereof, by a consideration of the following detailed description of the preferred embodiment. Reference will be made to the appended sheets of drawings, which will first be described briefly.

DETAILED DESCRIPTION OF THE PREFERRED EMBODIMENT

The present invention satisfies the need for a single display device that would permit display of both hardcopy and digital images. As further described below, the display device uses the same working surface to display either or both of these types of images. In the detailed description that follows, it should be appreciated that like element numerals are used to describe like elements illustrated in one or more of the figures.

Figures 1, 2, 3:
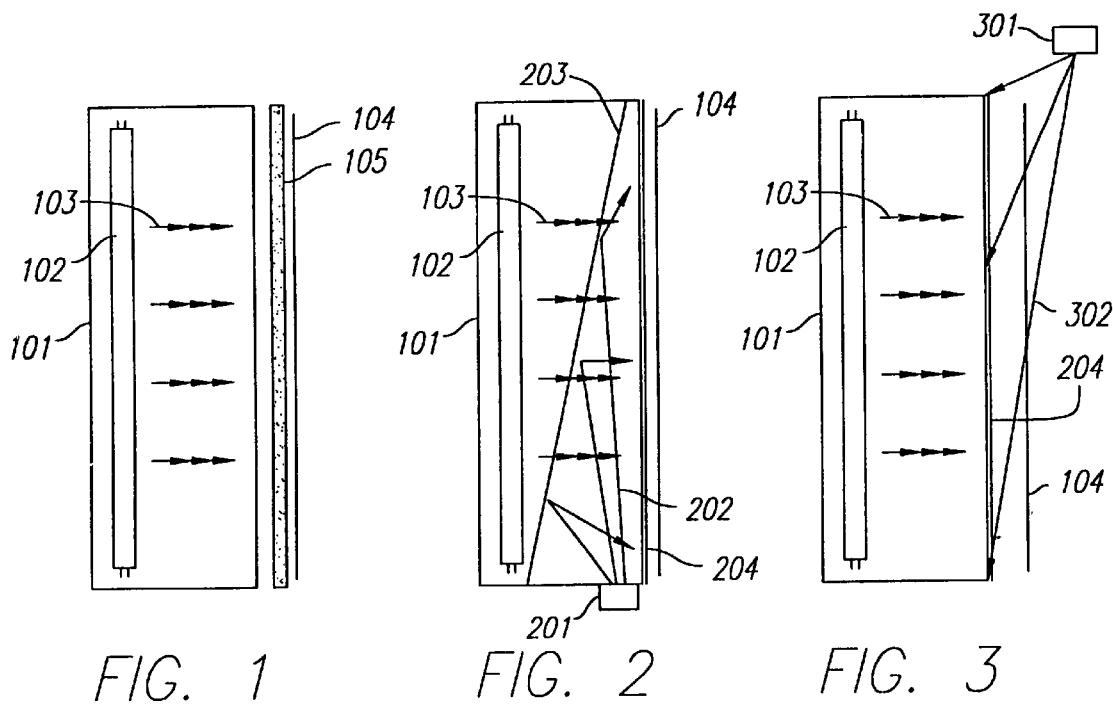
FIG. 1 is a schematic drawing of a viewing station in accordance with an embodiment of the present invention using backlighting for transillumination of hardcopy images, liquid crystal display (LCD) panel or other digital display device.
FIG. 2 is a schematic drawing of a viewing station in accordance with a second embodiment of the present invention using backlighting for transillumination of hardcopy images and back projection for digital imaging.
FIG. 3 is a schematic drawing of a viewing station in accordance with a third embodiment of the present invention using backlighting for transillumination of hardcopy images and front projection for digital imaging.

Referring first to FIG. 1, a first embodiment of a viewing station is illustrated. The viewing station comprises a housing 101 containing a light source 102. The light source 102 may be provided by one or more fluorescent tubes, cold cathode light, light emitting diodes (LEDs), plasma or other lighting sources. The housing 101 is substantially enclosed except for a front-facing surface on which a digital display panel 105 is disposed. The digital display panel 105 may be provided by an electroluminescent panel (ELP), a plasma display panel (PDP), a vacuum fluorescent display (VFD), an electro-chlomic display (ECD), a liquid crystal display (LCD), and the like. An exposed surface of the digital display panel 105 provides a mounting surface for attachment of a hardcopy image 104 thereto. The digital display panel 105 is translucent, permitting light emitted from the light source 102 (as represented by arrows 103) to pass therethrough in order to transilluminate the hardcopy image 104 in one mode of operation. In addition, the digital display panel 105 may be driven to display a digital image in another mode of operation.

The digital display panel 105 may be selectively driven to produce varying light densities that the viewer interprets as differing colors or shades of gray. The digital display panel 105 may further include an internal backlighting source ordinarily used for illuminating digital images displayed on the display panel, and which is controllable separately from the light source 102. For hardcopy image displaying, the digital display panel 105 can be used to control the amount of backlighting provided by the light source 102, in addition to the backlighting provided by the internal source. When driven in an "on" state, the digital display panel 105 will appear white or "clear" providing the most translucent condition in which backlighting will pass therethrough to transilluminate a hardcopy image 104. The amount of backlighting provided by the light source 102 is thus determined in part by the coefficient of translucency of the digital display panel 105 when in the "on" state.

Conversely, when driven in an "off" state, the digital display panel 105 becomes completely or nearly opaque. This allows the digital display panel 105 to act as a masking device when viewing a hardcopy image 104. This is especially important when viewing small hardcopy images on a large viewing area or when the diagnostician wishes to only view a small portion of a larger image. The viewing station may include preprogrammed mask sizes in which the digital display panel 105 is driven with a predetermined region in an "on" state with the remainder being in an "off" state. The preprogrammed mask sizes would correspond to known dimensions of hardcopy images. Alternatively, the viewing station may permit the generation of custom-shaped mask regions. In addition, by varying the degree in which the digital display panel 105 is driven between the "on" and "off" states, and/or by varying the light level provided by the light source 102, the amount of transillumination can be adjusted. A diagnostician may thereby select a desired level of transillumination in order to adjust for a particular range of densities of a hardcopy image 104.

The ability to vary the amount of backlighting provided by the light source 102 is also important in viewing digital images using the digital display panel 105. As with hardcopy viewing, higher levels of backlighting of digital display panels increase the perceived contrast levels of the displayed image. It is common practice to view digital images in rooms with low ambient lighting to maximize the value of the image. Thus, the ability to vary the backlighting provided by the light source 102 will also remove this environmental restriction and allow the greater dissemination of diagnostic quality viewing stations throughout the physical medical environment.

It should be appreciated that the embodiment of FIG. 1 is advantageous due to its simplicity and because it can be constructed from readily available materials. Nevertheless, a potential drawback of the embodiment of FIG. 1 is that conventional digital display panels are sensitive to high levels of heat, and the ability of a digital display panel to accurately display image information may be damaged or degraded when operating above a certain temperature. In the embodiment of FIG. 1, the light source 102 may generate an amount of heat that could be detrimental to the efficient operation of the digital display panel 105. Another potential drawback is that the coefficients of translucency of monochrome display panels are low and that of color display panels even lower.

FIG. 2 illustrates a second embodiment of a viewing station, which overcomes the drawbacks of the first embodiment. Unlike the first embodiment, the viewing station of FIG. 2 includes an image projector 201, a partially reflective surface 203, and a display screen 204. The partially reflective surface 203 is disposed within the housing 101 between the light source 102 and the display screen 204, and is disposed at an angle with respect to the display screen. The image projector 201 is disposed at a side of the housing 101, and is adapted to project a digital image that reflects off the partially reflective surface 203 onto the interior surface of the display screen 204 (as represented by arrows 202). The partially reflective surface 203 may be provided by a flat sheet of glass having a partially silvered surface. The display screen 204 provides a mounting surface for attachment of a hardcopy image 104 thereto.

As in the embodiment of FIG. 1, the light source 102 provides light to transilluminate a hardcopy image 104 affixed to the display screen 204. The light from the light source 102 passes through the partially reflective surface 203. When displaying digital images, the light source 102 would be lowered, turned off or blocked. The projected digital image passes from the projector 201 to the partially reflective surface 203 to the display screen 204. This embodiment is advantageous since it permits the overall depth of the housing 101 to be reduced. It should be appreciated that the projector 201 may be adapted to project the digital image onto the display screen 204 directly, such as from the rear of the housing 101, thereby eliminating the need for the partially reflective surface 203 altogether Since this embodiment does not use a digital display panel 105 as in FIG. 1, the heat generated by the light source 102 would present little or no detrimental effect.

In a further variation of the viewing station of FIG. 2, the light source 102 may be eliminated altogether, and the projector 201 would then be used to provide transillumination light as well as for projecting digital images. When providing transillumination, preset or user definable masks can be applied to the light before it leaves the projector 201. Combinations of transillumination light and digital images can also be projected by the projector 201. By virtue of the elimination of the light source 102, it therefore is unnecessary that the reflective surface 203 be adapted to transmit transillumination light therethrough.

FIG. 3 illustrates a third embodiment of a viewing station utilizing front projection of the digital image. A projector 301 is disposed separately from the housing 101 in front of or to the side of the display screen 204, so that it projects the digital image onto the front surface of the display screen (as represented by arrows 302). Unlike the second embodiment, the third embodiment does not include a partially reflective surface 203. A hardcopy image 104 may be affixed to the display screen 204 for transillumination in the same manner as the second embodiment.

Figure 4:
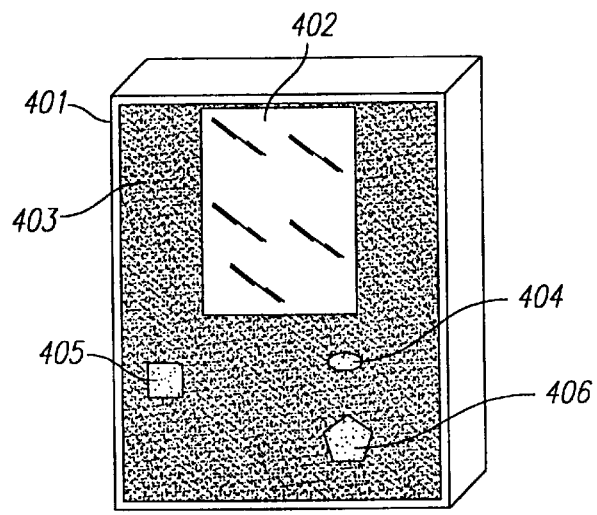
FIG. 4 is a perspective view of a viewing station in accordance with a fourth embodiment of the present invention using an electroluminescent panel (ELP) to selectively light different picture elements (pixels) at different intensities for masked backlighting for transillumination of hardcopy images and presentation of digital imaging.

A fourth embodiment of the viewing station is shown in FIG. 4, in which a display panel 401 is used to display both hardcopy and digital images. The front exposed surface of the display panel 401 provides a mounting surface for attachment of a hardcopy image thereto. The display panel 401 may also be driven with digital data to provide a digital image thereon. Specifically, the digital display 401 may be selectively driven to provide a rectangular "on" region 402, while the rest of the panel provides an "off" region 403. The "on" region 402 may comprise a preprogrammed mask size corresponding to the known dimensions of a hardcopy image, as in the first embodiment. The digital display 401 would provide sufficient luminosity to transilluminate a hardcopy image affixed to the front surface of the digital display. The digital display 401 may also be driven to provide various additional regions of variable luminosity (i.e., either "on" or "off" or in-between), such as the oval region 404, the square region 405, and the polygonal region 406. These additional regions may be used for transilluminating hardcopy images, or alternatively, may be used to display digital images to permit a direct comparison with a hardcopy image being transilluminated in the "on" region 402. It should be appreciated that the specific locations of these driven regions shown in FIG. 4 are entirely arbitrary, and a diagnostician may be provided with the ability to select and manipulate the specific location and size of the driven regions.

An example of a display panel providing sufficient luminescence for use as the digital display 401 is an electroluminescent panel (ELP), which comprises a grid of individually addressable pixel elements that have individually variable luminosity in order to provide both transillumination backlighting and digital image displaying. As known in the art, an ELP comprises an electroluminescent film, porous silicon or any light emitting material whose optical transmission properties can be altered by the application of an electric field can be used to form the light emitter. An ELP can provide transillumination ranging from 100% to 0%, and allow for multiple areas of varied shapes and intensities of transillumination. It should be appreciated that other types of digital displays having similar performance characteristics could also be advantageously utilized in this embodiment.

Figure 5:
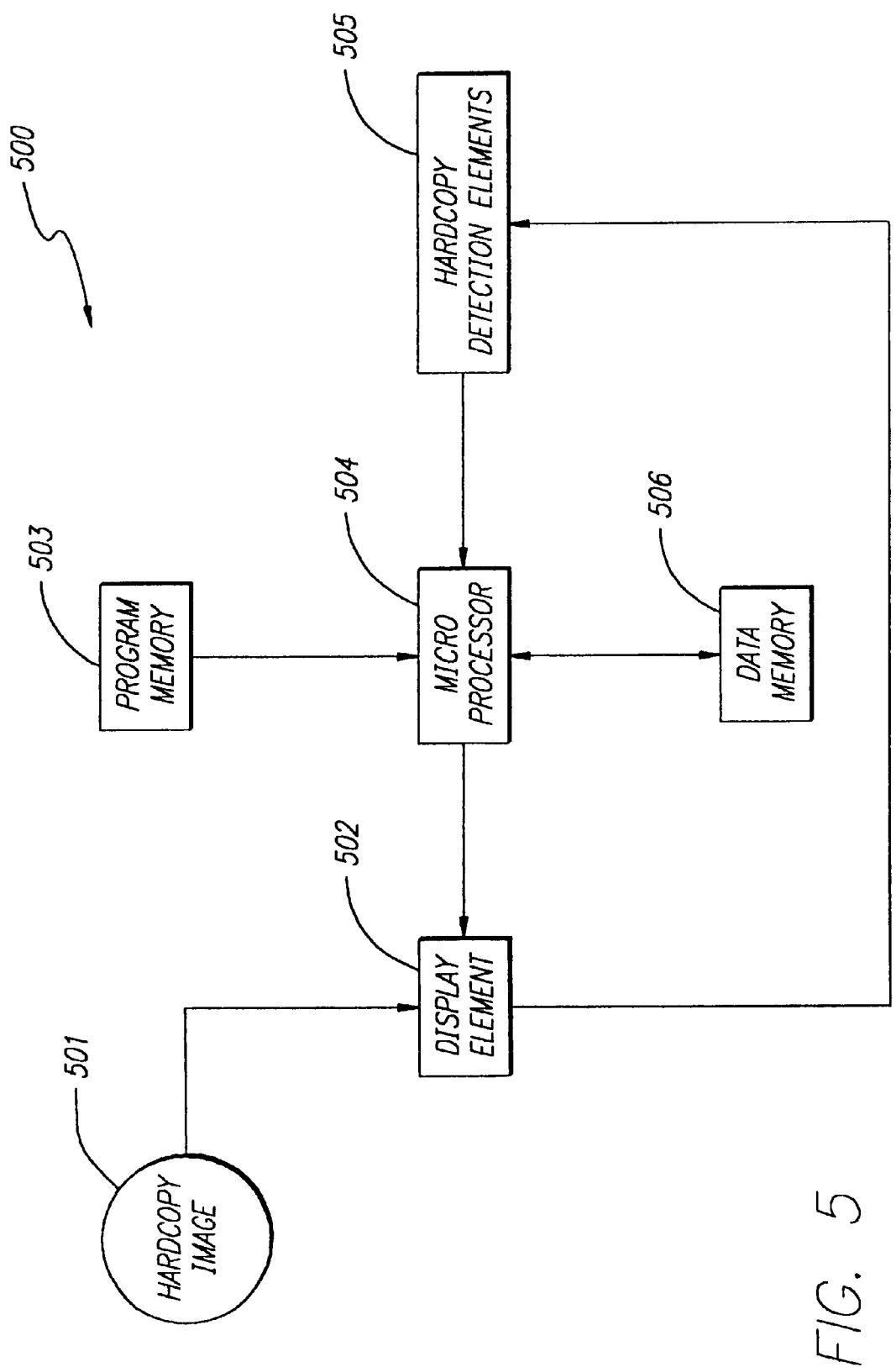
FIG. 5 illustrates a block diagram of a viewing system of the present invention.

Referring now to FIG. 5, an exemplary embodiment of a viewing station of the present invention is illustrated in block diagram form. The viewing system 500 includes a program memory 503, a processor 504, a data memory 506, a display element 502, and hardcopy image detector elements 505. The display element 502 may further include several lighting elements for backlighting of either the digital or hardcopy images, such as the light source 102 (FIGS. 1–3). In addition, the display element 502 may comprise various alternative display elements for displaying digital images, such as the digital display panel 105 (FIG. 1), the projectors 201 (FIG. 2), 301 (FIG. 3), or the ELP 401 (FIG. 4). The processor 504 is coupled to each of the program memory 503, data memory 506, display element 502, and hardcopy image detector elements 505, and controls operations of the viewing system in accordance with instruction sets, e.g., software or firmware, stored in the program memory 503. The processor 504 may be provided by a commercially available microprocessor, microcontroller, digital signal processor or custom fabricated application specific integrated circuit (ASIC). The program memory 503 may be of various types such as semiconductor-based read only memory (ROM), random access memory (RAM), or other memory devices commonly known to those skilled in the art. It should be apparent that the functions performed by the stored instruction set may also be accomplished by traditional hard wired circuits, but software or firmware systems are preferred due to their relative simplicity, adaptability to change, and low cost. To the extent that ROM devices are utilized for the program memory 503, the ROM devices may further be erasable or programmable so that modifications or revisions to the software can be implemented as desired. Moreover, other types of permanent storage media can be utilized as program memory 503, such as magnetic and optical disks. The data memory 506 may comprise RAM semiconductor devices.

As will be explained in more detail below, the processor 504 controls the activating of the digital image or the masking and lighting functions for viewing hardcopy images. The microprocessor 504 may also perform other operations, such as image manipulation for digital images, or viewing area adjustments based on input from hardcopy image detection elements 505. As discussed above, the viewing system 500 may be used to view both hardcopy and digital images. When viewing digital images, the processor 504 recalls the image from the data memory 506 to display the image on the display element 502. It should be apparent that the data memory 506 may be physically included in the viewing system 500 or outside the viewing system, as in the case of a computer network. In such an embodiment, the processor 504 may be used to retrieve data from a network data memory over a telecommunication link. When displayed, a diagnostician can manipulate the digital image using instructions contained in the program memory 503 and executed by the processor 504.

In the case of hardcopy viewing, a hardcopy image 501 may be physically placed on the display element 502 in a predetermined or random orientation. The hardcopy image 501 is detected on the display element 502 by the hardcopy detection elements 505, which notify the processor 504 of the presence of the hardcopy image. The display element 502 then operates to properly transilluminate the hardcopy image 501, such as by masking certain regions of the display element. In the foregoing embodiments in which the display element 502 is a digital display panel such as an LCD or ELP (i.e., FIGS. 1 and 4), masking is achieved by driving "off" the pixels of the masked region which blocks light from the backlight source. Similarly, in the foregoing embodiments in which a projector is used to project the digital image onto the display screen (FIGS. 2 and 3), masking is achieved by allowing light from the backlight source to only reach certain portions of the display element (such as using baffles). Alternatively, where rear projection is used (as in FIG. 2), masking may be achieved at the projector 201 by projecting masked light. These blocked portions can then be used for display of digital images by the projector 201.

Figure 6:
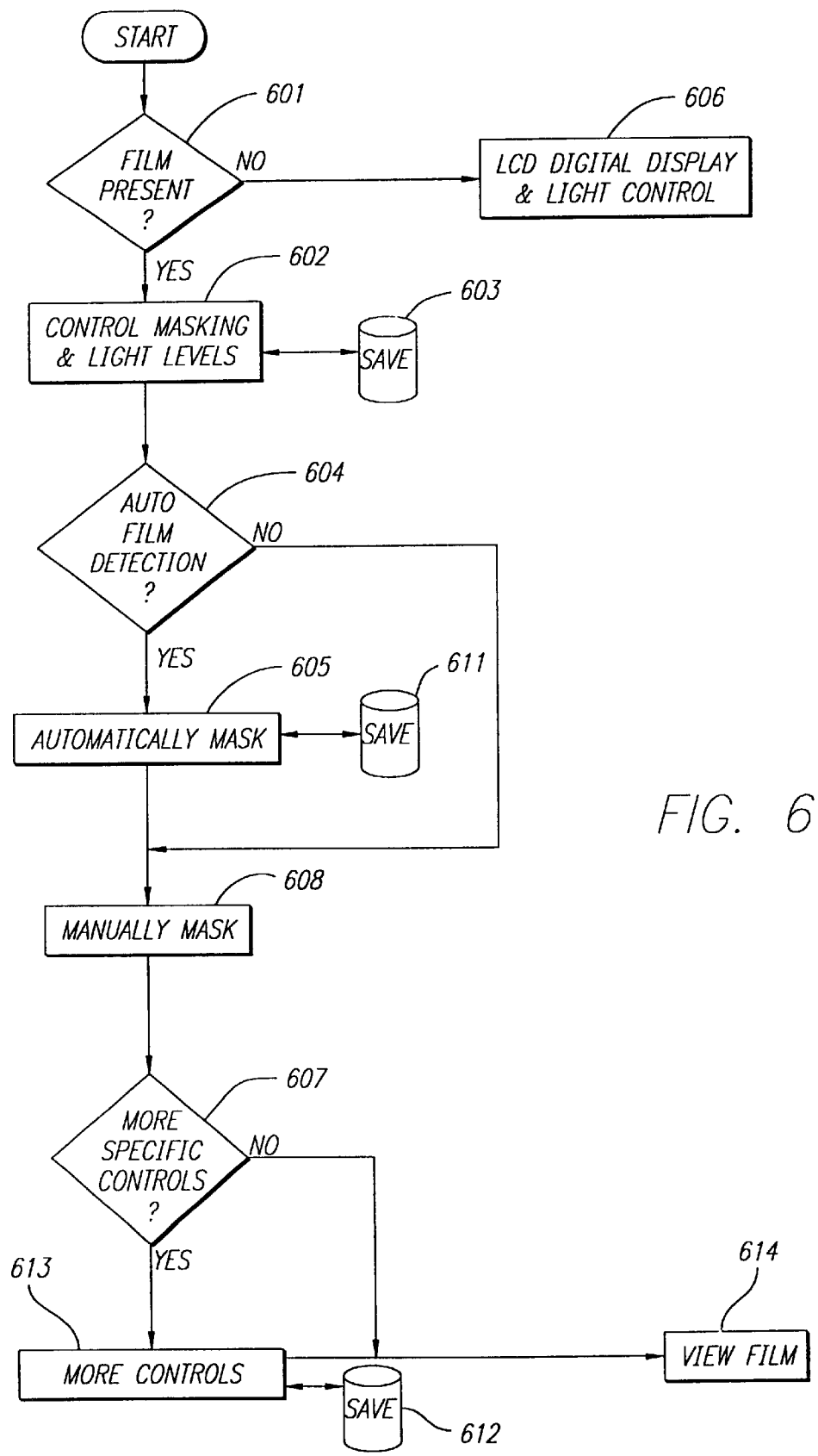
FIG. 6 illustrates an exemplary process for controlling operation of the viewing station of the present invention.

An exemplary logical process that the processor 504 executes in controlling the overall operation of the viewing station is shown in FIG. 6, with reference to the block diagram of FIG. 5. At step 601, the microprocessor 504 determines if a hardcopy image 501 is present on the surface of the display element 502. This can be done by a variety of known mechanical or electronic devices. For example, the display element 502 may include a hardcopy image-retaining device, such as a clip, disposed on one or more of the four sides that comprise the viewing surface. The hardcopy image-retaining device may further include a mechanical switch that toggles automatically when the hardcopy image is inserted into the hardcopy image-retaining device, or an optical sensor that detects the presence of the hardcopy image.

If it is determined that a hardcopy image is not present on the display element 502, then step 606 is executed in which the viewing station configures for digital display. More particularly, the microprocessor 504 would execute certain algorithms to permit a digital image to be retrieved from the data memory 506 and displayed by the display element 502. The algorithms may further permit the diagnostician to manipulate the digital image, including altering the brightness and contrast of the image, as well as the size and placement of the image on the display element 502. Moreover, the algorithms may further permit the diagnostician to enter comments regarding a displayed digital image that are stored in the data memory 506 along with the image data, or place labels or other indicia on the displayed digital image.

Conversely, if it is determined at step 601 that a hardcopy image is present on the display element 502, then step 602 is executed in which the viewing station configures for hardcopy image display. This process may be an automatic process whereby the viewing station automatically configures for display of a hardcopy image, or a manual process whereby the diagnostician has direct control over the configuration. As discussed above, the display element 502 could be used to produce different light levels and masking patterns. For example, the light transmissive properties of the display element 502 could be selectively increased or decreased, and the size and location of a masking region could be varied. Configuration files defining these particular parameters would be stored in the data memory 506 at step 603, and retrieved as required.

At step 604, a determination is made whether to execute an automatic hardcopy image detection process. This process may be selectable by the diagnostician, or may execute automatically. The hardcopy image detection process will determine the size and/or shape of a hardcopy image 501 affixed to the display element 502, and select the masking and control the light levels accordingly. The display element 502 may have sensing elements, such as a conventional touch screen, that detects the size and shape of the hardcopy image 501. Alternatively, the hardcopy image 501 may have specially encoded data defining the display parameters, such as within a bar code symbol or radio frequency identification (RFID) tag, that is scanned or read by the viewing station. In yet another alternative embodiment, the hardcopy detection elements 505 may comprise a series of mechanical detectors that determine the length of one side of the hardcopy image. As there are a finite number of common hardcopy image sizes, a look-up table could be used to determine the most likely missing measurement and automatically have the display element 502 mask to this size. Detectors on two perpendicular sides could be used to determine the precise hardcopy image sizes. Thereafter, the corresponding configuration files defining the size, shape and lighting parameters are retrieved from the data memory 506 at step 611 for execution by the microprocessor 504.

If the automatic hardcopy image detection process is not executed, the logical process shifts to step 608 at which a manual masking process is performed. The diagnostician may use a manual digit or stylus to identify areas of the display element 502 to be made more or less transmissive. For example, the diagnostician could circle an area of interest on the display element 502 and then request the surface outside this area become less transmissive, i.e., masked. Multiple patterns could be made in a similar manner, and such patterns and shapes could be saved in the data memory 506 for use at another time. Further, the display element 502 could be divided into two or more parts, some for viewing digital data and others for analog hardcopy image viewing. A graphic or other intuitive user interface, such as a digital pointer controlled by a computer mouse, could also be used to specify areas of more or less transmission, change the shape of the areas, and move the area over the viewing area.

Lastly, at step 607, a determination is made as to whether the diagnostician wants to perform additional manipulation and/or adjustments to the displayed image, such as to vary the backlight source. If so, step 613 is executed whereby certain additional algorithms are made available to the diagnostician. There may be stored subroutines, or macros, that are custom defined by the diagnostician and retrieved from the data memory 506 at step 612. As part of the additional manipulations, the diagnostician may be able to retrieve other data files from the data memory 506, such as a patient information file containing textual information. In this regard, the data memory 506 may be integrated with or connected to a hospital information system or network in which such patient information is stored. The textual information may thereby be displayed on the display element 502 alongside a hardcopy or digital image. The diagnostician may further be able to edit or annotate the patient information file as part of the additional manipulations of step 613. Once the additional manipulation and/or adjustments are performed, the parameters may be stored in the data memory 506 for later use with a particular hardcopy image should a second review of that image be desired, or for later review of a similar type of image. If no further manipulation is desired, the diagnostician may view the hardcopy image 501 at step 614.

It should be appreciated that the entire viewing station may be contained within a single unit. Alternatively, the individual elements of the viewing station may be distributed. For example, a simple unit may be used to display analog images, a separate unit used to project digital images, and a third unit used to process information for masking purposes. The masking information can be transmitted to an attached computer, stored locally for later transfer, or forwarded to an application program resident within the viewing station itself. This separation of elements indicates how traditional hard copy viewboxes can be upgraded or retrofitted to provide for digital viewing by the addition of digital display devices and associated control elements. For example, in FIG. 1, the digital display panel 105 may be added to an existing analog viewbox that includes the housing 101 and light source 102.

There are many alternative ways to determine the size of the hardcopy image 501 being displayed for masking purposes (i.e., step 605 of FIG. 6). In a first alternative embodiment, plural LEDs can be mounted in the hardcopy image-retaining device that can send light to optical sensors mounted in the viewing surface (or visa versa). The number of sensors not receiving the full or expected amount of light could then be used to determine the length of the hardcopy image. In a similar manner, two or more of the sides of the viewing surface can include hardcopy image-retaining devices with LED/sensor pairs. By mounting the hardcopy image in such a manner as to engage two or more of the sides, the hardcopy image size can be determined. This is even true in the case where three corners of the hardcopy image interact with three sensors in three different retaining bars.

Figure 7:
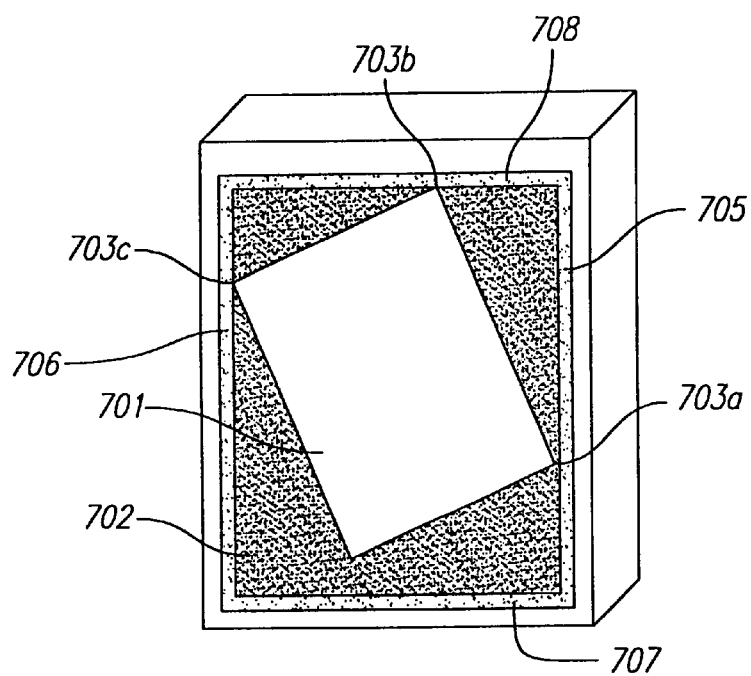
FIG. 7 is a perspective view of a viewing station illustrating an alternate method for controlling the masking of light by the controlling operation of FIG. 6.

For example, as shown in FIG. 7, a hardcopy image 701 is placed on the display panel 702 in an unexpected, angled position. The display panel 702 has vertical image-retaining devices 705, 706 and horizontal image-retaining devices 707, 708. Due to the orientation of the hardcopy image 701, three corners 703a, 703b, 703c of the hardcopy image 701 intersect the sensors in three different image-retaining devices 705, 708, 706, respectively. Since the hardcopy images have certain known, standard sizes, the orientation of the hardcopy image 701 can be readily determined from the three data points to data stored in a look-up table, and the "off" and "on" regions illuminated accordingly. Similarly, in the case where only two corners make contact with different retaining bars, the approximate "off" and "on" regions can be determined in the same manner.

In another embodiment, a combination of vertical touch bars disposed along the edge of the device (but not on the viewing surface) and horizontal image-retaining devices could be utilized. The vertical touch bars could be used to determine the length of a hardcopy image. When combined with sensors in the horizontal hardcopy image-retaining device, the overall size of the hardcopy image could be determined.

Figure 8:
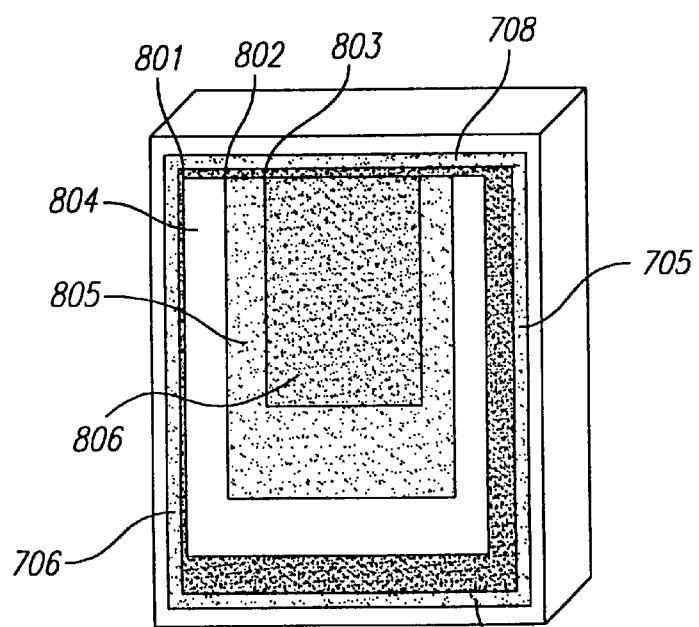
FIG. 8 is a perspective view of a viewing station illustrating another alternative method for controlling the masking of light by the controlling operation of FIG. 6.

In yet another embodiment, one of the image-retaining devices 705–708 could be provided with a series of pressure or optical sensors. Each sensor could correspond to a notch or visual cue identifying its location and the corresponding hardcopy image size for which it will activate a mask size. For example, as shown in FIG. 8, an 8"×10" size hardcopy image 804 might correspond with a first visual cue 801, a 6"×7" hardcopy image 805 corresponds with a second visual cue 802, and a smaller size hardcopy image 806 corresponds with a third visual cue 803. By placing one edge of a hardcopy image over a given one of the sensors, the corresponding mask and transillumination pattern could be displayed. The order of the sensors and the sizes of hardcopy images they correspond to can be set so that multiple sensors could be activated without displaying the wrong masking format. For example, ordering the sensors from left to right to correspond from largest to smallest sized hardcopy images will accomplish this function. As shown in FIG. 8, the largest hardcopy image covers multiple sensors, while smaller hardcopy images cover decreasing numbers of sensors.

As noted above, the image retaining devices 705–708 could further include optical sensors adapted to read encoded indicia, such as bar code symbols, formed on the hardcopy images. The encoded indicia may define the desired display parameters for the hardcopy image, and would cause the display panel to automatically configure for the particular hardcopy image.

In still another embodiment, an optical sensing device such as a bank of photo-sensors or a digital camera can be placed along the top, bottom or sides of a viewing device so as to focus on certain points of the viewing surface. In this manner, the optical sensing device can "see" the designated points of the viewing surface covered by one or more hardcopy images and use this information to adjust the display element to act as a masking device. Similarly, the optical sensing device can be focused on the back surface of the viewing area. By measuring the amount of reflective light from this surface it would be possible to determine the size and location of one or more hardcopy images in contact with the other side of the viewing surface. In a similar embodiment, an angled mirror could be trained on the viewing surface. A reflected image could thereby be relayed to an optical sensing device remote from the viewing surface to determine the position of one or more hardcopy images placed on the viewing surface.

In yet another embodiment, a touch panel could be placed over the viewing surface in association with hardcopy image-retaining bars (described above). Sensors in the image-retaining bars would measure the length of an edge of a hardcopy image, as described previously. Then, by touching either of the lower corners of the hardcopy image, the size of the image could be determined. Alternatively, if a corner of a displayed hardcopy image was always inserted at a specific point in the hardcopy image-retaining bar, and a diagnostician placed a single touch on the screen at the opposite lower corner of the hardcopy image, the overall size of the hardcopy image could be determined. It should be appreciated that this embodiment does not require measuring of the image length by the image-retaining bar sensor.

From these examples, many other combinations could be devised by one skilled in the art and knowledgeable of other detection devices without departing from the spirit and scope of this invention. Once the approximate hardcopy image size is determined, the same algorithms and logical control process described before could be used to further refine the transmissive properties of the viewing surface and the shape and size of the mask. These custom settings could be saved for use at another time with the same or a different hardcopy image. It should be noted that each of the masking and shaping algorithms can be used independently from each other or together and in random order. It is possible to envision a skilled user of such a system moving directly to the most specific controls.

Having thus described a preferred embodiment of a display device for both hardcopy and digital images, it should be apparent to those skilled in the art that certain advantages of the aforementioned system have been achieved. It should also be appreciated that various modifications, adaptations, and alternative embodiments thereof may be made within the scope and spirit of the present invention. The invention is further defined by the following claims.

What is claimed is:

1. An image viewing station, comprising:
   a housing having an internal light source;
   a light transmissive display panel coupled to a portion of said housing such that light provided from said internal light source passes through said display panel, said display panel further comprising an outer surface adapted to receive a hardcopy image thereon, said hardcopy image being transilluminated by said light passing through said display screen; and
   a projector adapted to project a digital image onto said display panel;
   wherein an operator of said image viewing station can selectively display one or both of said hardcopy image and said digital image on said display panel.

2. The image viewing station of claim 1, further comprising a partially reflective surface disposed between said light source and said display panel, said digital image projected by said projector reflecting off of said partially reflective surface and onto an inner surface of said display panel.

3. The image viewing station of claim 1, wherein said digital image is projected directly onto said outer surface of said display panel from said projector.

4. The image viewing station of claim 1, wherein said digital image is projected directly onto an inner surface of said display panel from said projector.

5. The image viewing station of claim 1, further comprising means for masking a portion of said display panel surrounding said hardcopy image.

6. The image viewing station of claim 1, further comprising means for detecting at least one of size and position of said hardcopy image on said display panel.

7. The image viewing station of claim 1, further comprising means for selectively varying an amount of transillumination of said hardcopy image.

8. The image viewing station of claim 1, further comprising a processor and a memory containing stored digital image data and stored instructions that are executed by said processor, said processor controlling operation of said display panel and said projector.

9. The image viewing station of claim 8, wherein said stored instructions cause said processor to perform the step of controlling illumination levels of said display panel.

10. The image viewing station of claim 8, wherein said stored instructions cause said processor to perform the step of detecting presence of said hardcopy image on said display panel.

11. The image viewing station of claim 8, wherein said stored instructions cause said processor to perform the step of detecting size and/or position of said hardcopy image on said display panel.

12. The image viewing station of claim 8, wherein said stored instructions cause said processor to perform the step of selecting a preprogrammed mask size for said hardcopy image.

13. The image viewing station of claim 8, wherein said stored instructions cause said processor to perform the step of permitting manual control over a mask size for said hardcopy image.

14. The image viewing station of claim 8, wherein said stored instructions cause said processor to display textual information on said display panel as said digital image.

15. The image viewing station of claim 8, wherein said stored instructions cause said processor to retrieve a data file containing information relating to a hardcopy or digital image.

16. The image viewing station of claim 1, wherein said projector is further adapted to project textual information onto said display panel.

17. The image viewing station of claim 1, further comprising means for detecting optical indicia disposed on said hardcopy image, said optical indicia defining viewing parameters for said hardcopy image.

18. An image viewing station, comprising:
    a housing;
    a light transmissive display panel coupled to a portion of said housing, said display panel further comprising an outer surface adapted to receive a hardcopy image thereon; and
    a projector adapted to project light including a digital image onto said display panel, said light provided from said projector passing through said display panel, said hardcopy image being transilluminated by said light passing through said display screen;
    wherein an operator of said image viewing station can selectively display one or both of said hardcopy image and said digital image on said display panel.

19. The image viewing station of claim 18, further comprising a light source disposed within said housing.

20. The image viewing station of claim 19, further comprising a partially reflective surface disposed between said light source and said display panel, said digital image projected by said projector reflecting off of said partially reflective surface and onto an inner surface of said display panel.

21. The image viewing station of claim 18, wherein said digital image is projected directly onto said outer surface of said display panel from said projector.

22. The image viewing station of claim 18, wherein said digital image is projected directly onto an inner surface of said display panel from said projector.

23. The image viewing station of claim 18, further comprising means for masking a portion of said display panel surrounding said hardcopy image.

24. The image viewing station of claim 18, further comprising means for detecting at least one of size and position of said hardcopy image on said display panel.

25. The image viewing station of claim 18, further comprising means for selectively varying an amount of transillumination of said hardcopy image.

26. The image viewing station of claim 18, further comprising a processor and a memory containing stored digital image data and stored instructions that are executed by said processor, said processor controlling operation of said display panel and said projector.

27. The image viewing station of claim 26, wherein said stored instructions cause said processor to perform the step of controlling illumination levels of said display panel.

28. The image viewing station of claim 26, wherein said stored instructions cause said processor to perform the step of detecting presence of said hardcopy image on said display panel.

29. The image viewing station of claim 26, wherein said stored instructions cause said processor to perform the step of detecting size and/or position of said hardcopy image on said display panel.

30. The image viewing station of claim 26, wherein said stored instructions cause said processor to perform the step of selecting a preprogrammed mask size for said hardcopy image.

31. The image viewing station of claim 26, wherein said stored instructions cause said processor to perform the step of permitting manual control over a mask size for said hardcopy image.

32. The image viewing station of claim 26, wherein said stored instructions cause said processor to display textual information on said display panel as said digital image.

33. The image viewing station of claim 26, wherein said stored instructions cause said processor to retrieve a data file containing information relating to a hardcopy or digital image.

34. The image viewing station of claim 18, wherein said projector is further adapted to project textual information onto said display panel.

35. The image viewing station of claim 18, further comprising means for detecting optical indicia disposed on said hardcopy image, said optical indicia defining viewing parameters for said hardcopy image.

* * * * *